US006471633B1

(12) United States Patent
Freed

(10) Patent No.: US 6,471,633 B1
(45) Date of Patent: Oct. 29, 2002

(54) MECHANICAL AUXILLARY VENTRICLE BLOOD PUMP WITH REDUCED WAIST PORTION

(75) Inventor: Paul S. Freed, Bloomfield Hills, MI (US)

(73) Assignee: L.Vad Technology, Inc., Detroit, MI (US)

( * ) Notice: Subject to any disclaimer, the term of this patent is extended or adjusted under 35 U.S.C. 154(b) by 0 days.

(21) Appl. No.: 09/379,475

(22) Filed: Aug. 23, 1999

(51) Int. Cl.$^7$ .............................................. A61M 1/12
(52) U.S. Cl. ........................... 600/16; 600/18; 623/3.21
(58) Field of Search ...................... 600/16, 18; 623/3.1, 623/3.16, 3.21, 3.26

(56) References Cited

U.S. PATENT DOCUMENTS

| 4,051,840 A | * | 10/1977 | Kantrowitz et al. ........... 128/1 |
| 4,630,597 A | * | 12/1986 | Kantrowitz et al. ........... 128/1 |
| 4,976,729 A | * | 12/1990 | Holfert et al. ................. 623/3 |
| 6,214,022 B1 | * | 4/2001 | Taylor et al. ............... 606/153 |

* cited by examiner

Primary Examiner—Kennedy Schaetzle
(74) Attorney, Agent, or Firm—Young & Basile, P.C.

(57) ABSTRACT

An apparatus adapted to be inflated and deflated in response to selective communication with a source of pressurized fluid includes a bladder having a semi-rigid shell body portion and a relatively thin membrane portion defining an inflatable chamber. The elongate semi-rigid shell body preferably includes a contoured, concave inner surface terminating at a peripheral side edge. At least one passage extends through the shell body defining an opening in the inner surface of the shell body. The flexible membrane is continuously bonded to the shell body adjacent the peripheral side edge to define the enclosed inflatable chamber in communication with the passage. The membrane has a reduced waist portion defining a membrane tension zone adjacent the opening of the passage into the chamber to reduce the probability of occluding the entrance while deflating the chamber.

19 Claims, 3 Drawing Sheets

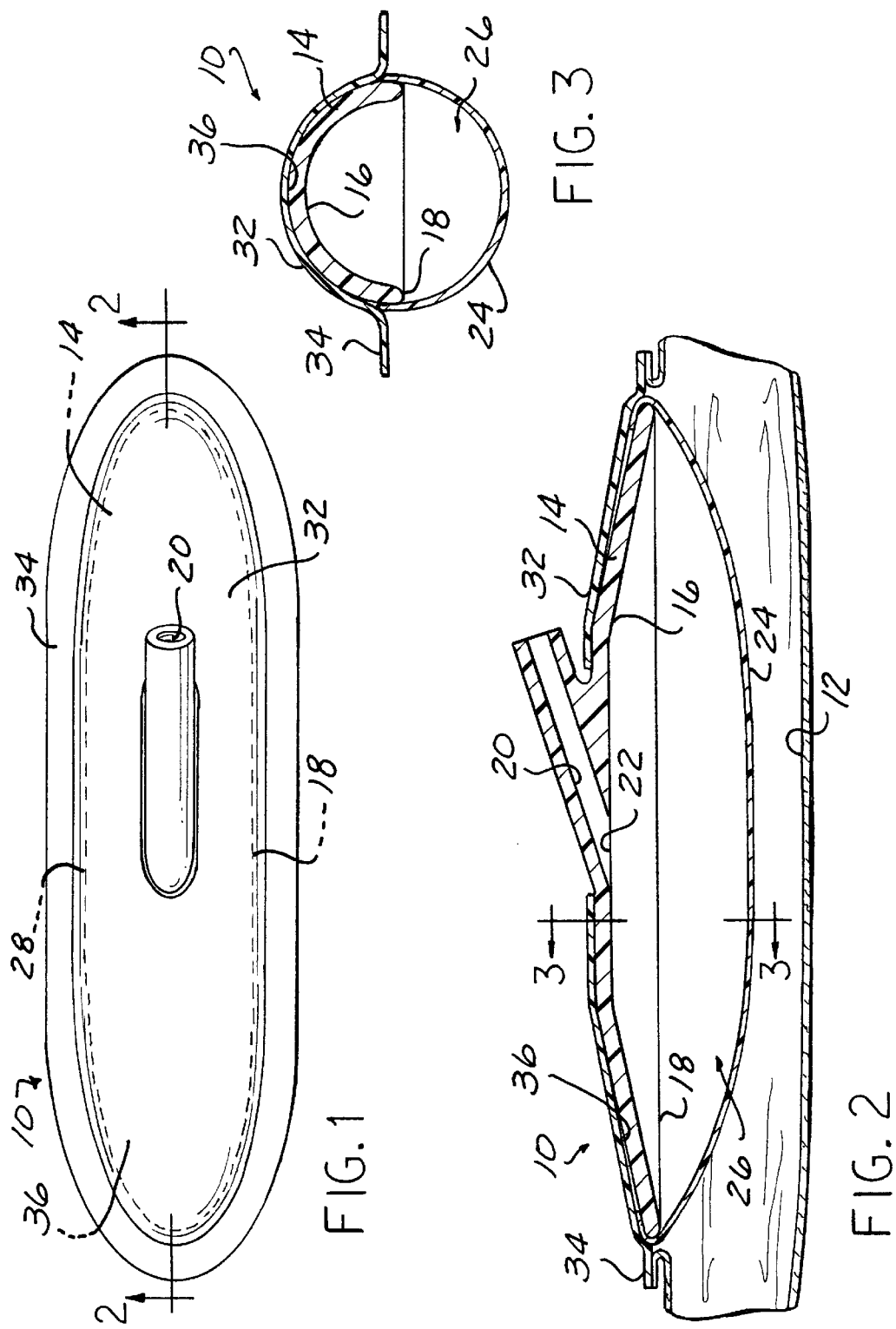

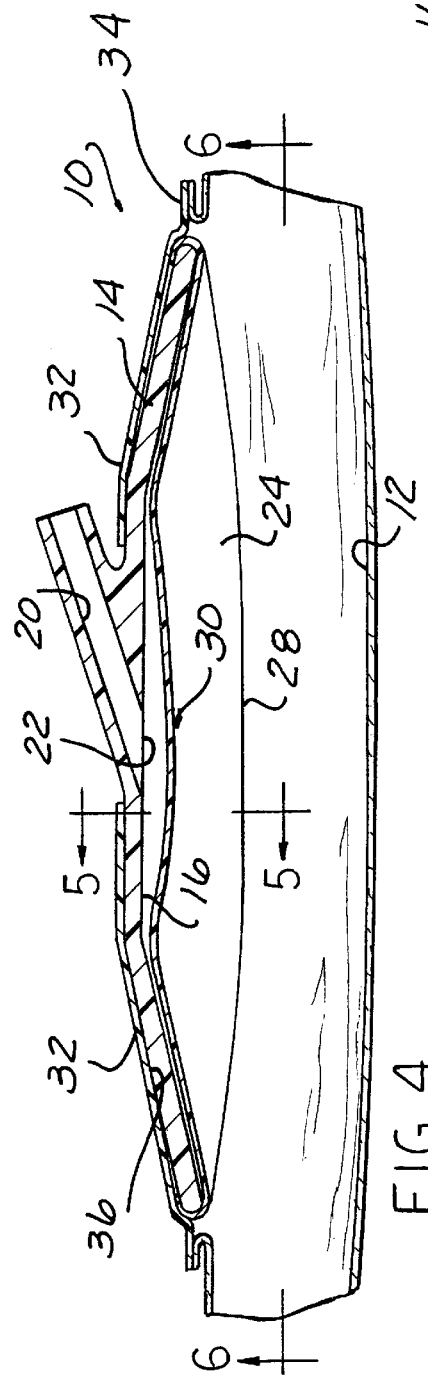
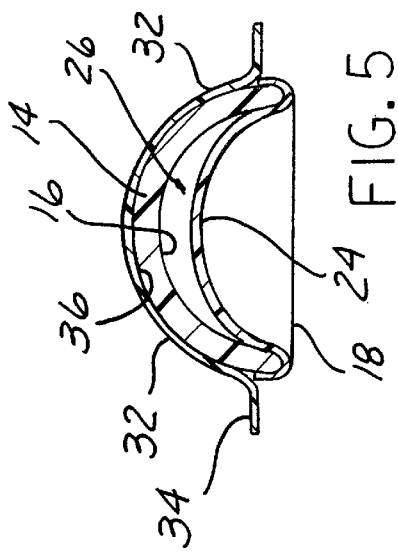
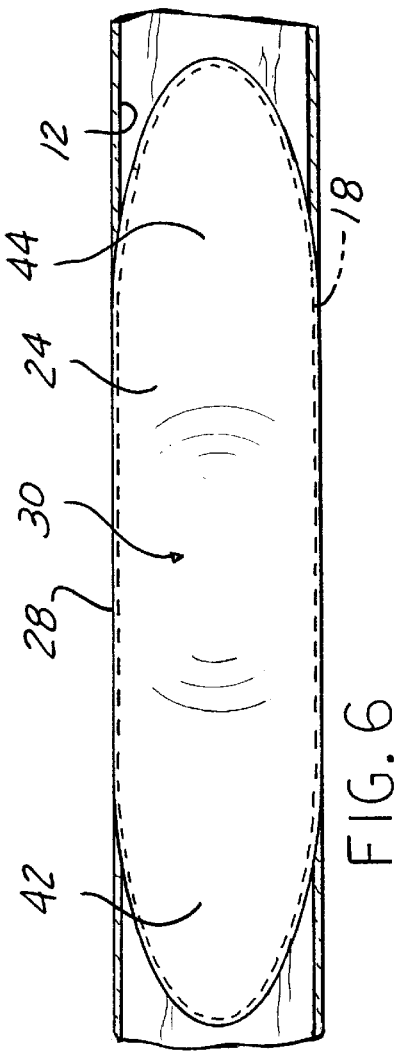

MECHANICAL AUXILLARY VENTRICLE BLOOD PUMP WITH REDUCED WAIST PORTION

FIELD OF THE INVENTION

The present invention relates to a dynamic aortic patch for assisting cardiac function during a cardiac cycle of a patient when positioned with respect to an aorta of the patient, and in particular, to a dynamic aortic patch or blood pump with a reduced waist portion to reduce the probability of occluding an port to the inflatable chamber of the pump.

BACKGROUND OF THE INVENTION

A dynamic aortic patch is permanently surgically implanted in the wall of the aorta to augment the pumping action of the heart. It is sometimes referred to as a mechanical auxiliary ventricle (MAV) or described as a permanent balloon pump.

Typically, the device includes a flexible bladder which is inflated and deflated in a predetermined synchronous pattern with respect to the diastole and systole of the patient to elevate aortic blood pressure immediately after aortic valve closure. Inflation and deflation of the bladder is accomplished by means of a supply tube connected to the bladder and to a percutaneous access device (PAD). The PAD is permanently surgically implanted in a patient's body to provide a through-the-skin coupling for connecting the supply tube to an extra-corporeal fluid pressure source. Electrical leads from electrodes implanted in the myocardium are likewise brought out through the skin by means of the PAD. The "R" wave of the electrocardiograph can be employed to control the fluid pressure source to inflate and deflate the inflatable chamber in a predetermined synchronous relationship with the heart action.

The dynamic aortic patch acts to assist or augment the function of the left ventricle and is typically restricted to use in patients who have some functioning myocardium. The dynamic aortic patch does not need to be operated full-time, and in fact, is usually operated periodically on a scheduled on-time, off-time regimen. Typically, the patient can be at least temporarily independent of the device for periods of one to four hours or more, since the dynamic aortic patch does not require continuous operation.

The present invention is directed to an improvement over prior known dynamic aortic patches, for example as disclosed in U.S. Pat. No. 4,630,597. This patent discloses a device with an elongate bladder, where one longitudinal side is formed with a relatively thick, semi-rigid, inwardly concave wall. The semi-rigid wall is integrally joined to a relatively thin and flexible wall of the bladder. A layer is bonded to the outer side of the semi-rigid wall portion of the bladder and cut with a freely projecting peripheral edge portion to provide a suture flange for suturing the device in place within an incision in the aorta. A connecting tube is integrally formed on the semi-rigid wall portion and projects outwardly therefrom for connecting the lumen of the bladder to a pneumatic or other pressurized fluid supply source. The inner surface of the semi-rigid portion of the bladder is concave in shape and formed with a plurality of grooves extending from the supply tube opening outwardly to the periphery of the semi-rigid portion to prevent entrapment of air bubbles within the bladder as the bladder is being deflated.

It would be desirable to provide a dynamic aortic patch that did not require the formation of a plurality of grooves extending from the supply tube opening and outwardly toward the periphery. It would be desirable to provide a dynamic aortic patch that prevents, or reduces the possibility of, occluding the entrance to the inflatable chamber while deflating the chamber. It would be desirable to provide a dynamic aortic patch with a flexible membrane with different tension zones along its longitudinal length. It would be desirable to provide a dynamic aortic patch having a higher tension zone of the flexible membrane adjacent the opening of the passage into the inflatable chamber.

SUMMARY OF THE INVENTION

In the preferred embodiment of the present invention, the construction of a dynamic aortic blood pump or mechanical auxiliary ventricle (hereafter MAV) includes an elongate semi-rigid shell member having a concave inner surface and a flexible membrane integrally bonded to the outer peripheral surface of the shell member to define a chamber between the concave inner surface and the membrane. When the MAV is sutured into the descending aorta in the thoracic or abdominal cavity it will present an elongate elliptical septum (the membrane) which is caused to expand into the aorta under fluid pressure during an inflation cycle and displaces blood with an elongate semi-prolate spheroid bulging of the membrane projecting from the shell perimeter. In the deflation cycle the hydraulic (aortic blood) forces on the membrane typically cause the central portion of the membrane (the most supple region with the maximal aortic lumen intrusion) to collapse toward the shell concavity first. The fluid pressure inlet (outlet) tube leading to the internal passageway of the chamber is located centrally and could be prematurely occluded by the aforementioned membrane collapsibility (preventing full deflation). Prior devices, such as that disclosed in U.S. Pat. No. 4,630,597 disclose the use of a plurality of grooves that extend from the opening of the internal passage that prevent the passage from being prematurely occluded. Another prior known device disclosed in U.S. Pat. No. 4,051,841 teaches the use of a system of longitudinal filaments to prevent fluid entrapment under similar circumstances.

The pumping efficiency of the MAV is substantially reduced by this partial deflation, created when a portion of the air in the chamber is trapped by the premature occlusion of the inlet passage. The full stroke typical displacement capability of 35 cc (cubic centimeters) based on the membrane seating on the shell concavity would be reduced by the percentage volume of air entrapment were it not for the system of grooves that extended over the length of the MAV as disclosed in U.S. Pat. No. 4,630,597.

However, the system of grooves creates long term problems of membrane durability associated with the localized flexing of the membrane at each groove site, when it is hydraulically driven against the shell concavity (by aortic blood pressure) especially at high pulsing rates. The shell and membrane materials tend to be low slip, high grab substances that will create localized rubbing and heating along the groove ridges and when combined with the plurality of groove flexing and stretch sites can lead to membrane distortion and failure even in the presence of a surface lubricant. Furthermore, while the grooves prevent occlusion of the air outlet passage the grooves can create some delay in deflation by requiring exhausting air to travel through the long groove passageways formed if the membrane seats first in the central region of the shell concavity. A related problem concerns "slapping" or the thumping associating with the supple membrane being accelerated against the shell concavity.

The problems associated with occlusion prevention groove geometry in the MAV are eliminated by the present invention, which does not employ a groove system but makes use of preferential stretching modes built into the membrane geometry and which is conveniently referred to as a "waist". The waist consists of carefully graduated narrowing of the membrane mid-body that shortens the arcuate cord length so as to prevent the membrane from bottoming out against the shell concavity in the mid-zone of the MAV and thus permitting the unhindered exhausting of air from all of the MAV chamber. In this mode of operation occlusion of the air outlet is prevented, without resort to a groove system and its associated problems.

The MAV is essentially a bladder, and bladders along with elastomeric diaphragms find wide application outside of heart assist applications. Bladder and diaphragm devices are used as clamping and jacking or lifting devices as well as pumping and cushioning devices and as low pressure sensors. The problem of exhaust air entrapment is a universal one and the "waist" concept is believed to be applicable especially for bladders of a longitudinal configuration which are in widespread usage.

A dynamic aortic patch or blood pump according to the present invention assists cardiac function during a cardiac cycle of a patient when positioned with respect to an aorta of the patient. The dynamic aortic patch or mechanical auxiliary ventricle includes an elongate semi-rigid shell having a contoured, concave inner surface terminating at a peripheral side edge. At least one passage extends through the shell to define an opening in the inner surface. A flexible membrane is continuously bonded to the shell adjacent the peripheral side edge to define an enclosed inflatable chamber in communication with the passage. The membrane has a reduced waist portion defining a membrane tension zone adjacent the opening of the passage into the chamber to prevent occluding the entrance while deflating the chamber.

The present invention also includes an apparatus for forming the flexible membrane for the dynamic aortic patch. The apparatus includes an elongate mandrel having a shape defined by substantially flat major surfaces opposite from one another and terminating at a rounded peripheral side edge extending between the major surfaces. The side edge is contoured and curved to define partial ellipses at both ends and a reduced waist portion adjacent a midway position. The mandrel is adapted to receive the thin, flexible, heat setable, membrane over one of the flat major surfaces and wrapped around the side edge a sufficient distance to form a flange adjacent to the opposite flat major surface. At least one clip can also be provided for holding the membrane in position during a heating process to set a defined shape into the memory of the membrane, where the shape corresponds to the shape of the mandrel.

A method of manufacturing a dynamic aortic patch according to the present invention includes the steps of providing an elongate mandrel having a shape defined by substantially flat major surfaces opposite one another and terminating at a rounded peripheral side edge extending between the major surfaces. The side edge is contoured and curved to define partial ellipses at both ends and a reduced waist portion adjacent a midway portion. The method also includes the step of placing a thin, flexible, heat setable membrane over one of the flat major surfaces and wrapping the membrane around the side edge a sufficient distance to form a flange adjacent the opposite flat major surface. At least one clip is provided for holding the membrane in place on the mandrel. The method includes the step of heating the membrane sufficiently to set the shape of the mandrel in the membrane. An elongate semi-rigid shell is provided having a contoured, concave inner surface terminating at a peripheral side edge and at least one passage extending through the shell to define an opening in the inner surface. The method also includes the step of permanently attaching the flange of the membrane to the shell adjacent the peripheral side edge to define an inflatable chamber in fluid communication with the at least one passage defining an opening in the inner surface of the shell.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 1 is a plan view of a mechanical auxiliary ventricle blood pump with reduced waist portion according to the present invention;

FIG. 2 is a cross-sectional view taken as shown in FIG. 1 illustrating the blood pump or dynamic aortic patch in an inflated position and sutured to the wall of an aorta of a patient;

FIG. 3 is a cross section view taken as shown in FIG. 2 illustrating the dynamic aortic patch in the inflated condition;

FIG. 4 is a cross-sectional view similar to that illustrated in FIG. 2 with the blood pump or dynamic aortic patch in a deflated condition;

FIG. 5 is a cross section view taken as shown in FIG. 4 illustrating the dynamic aortic patch in a deflated condition;

FIG. 6 is a bottom view of the dynamic aortic patch illustrating the reduced waist portion, membrane septum and membrane tension zone according to the present invention;

DESCRIPTION OF THE PREFERRED EMBODIMENT

Figure 7:
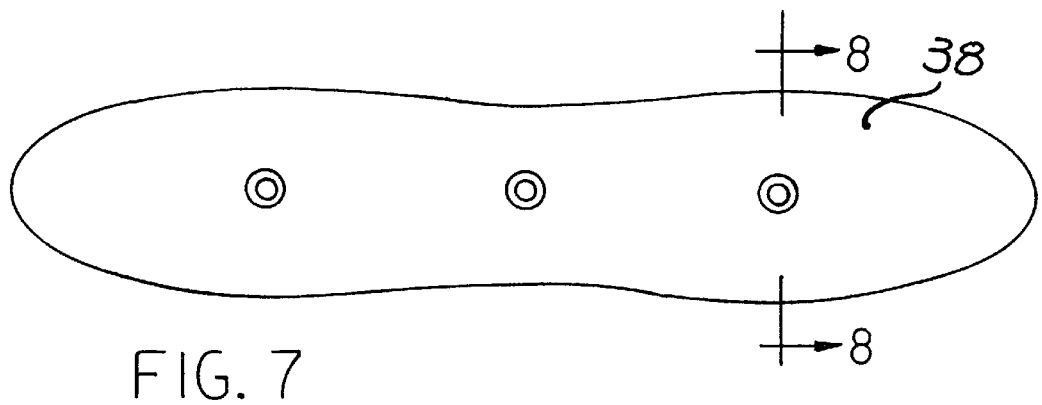
FIG. 7 is a plan view of a mandrel for forming a flexible membrane into a predefined shape according to the present invention.

A dynamic aortic patch, mechanical auxiliary ventricle or blood pump, generally designated as 10 is illustrated in FIGS. 1–6. The dynamic aortic patch 10 according the present invention assists in cardiac function during a cardiac cycle of a patient when positioned with respect to an aorta 12. The dynamic aortic patch 10 preferably includes an elongate, semi-rigid shell 14 having a contoured, concave inner surface 16 terminating at a peripheral side edge 18. At least one passage 20 extends through the shell 14 to define an opening 22 in the inner surface 16. An elongate, flexible membrane 24 is continuous bonded to the shell 14 adjacent to the peripheral side edge 18. The flexible membrane 24 in cooperation with the shell 14 defines an enclosed inflatable chamber 26 in fluid communication with the passage 20. As best seen in FIGS. 4 and 6, the membrane 24 has a reduced waist portion 28 defining a membrane tension zone 30 adjacent the opening 22 of the passage 20 through the shell 14. The reduced waist portion 28 or membrane tension zone 30 prevents the membrane 24 from occluding the entrance while deflating the inflatable chamber 26.

A piece of sheet material 32 of a commercially available type and certified for use in implanted devices, or other suitable material, is bonded to one side of the shell 14. The sheet material 32 is cut generously to provide a peripheral hem or flange 34. The flange 34 projects freely from the shell 14 to provide a suture flange for implanting the device in an incision in the aorta 12. As previously indicated, the inflatable chamber 26 is formed with an integral projecting tube portion or passage 20 with a distal end connected to one end of a supply tube (not shown).

Further details regarding the structure and function of the dynamic aortic patch and associated devices and controls can be obtained from U.S. Pat. No. 4,630,597 issued Dec. 23, 1986; U.S. Pat. No. 4,634,422 issued Jan. 6, 1987; U.S. Pat. No. 5,242,415 issued Sep. 7, 1993; U.S. Pat. No. 5,833,619 issued Nov. 10, 1998 and U.S. Pat. No. 5,833,655 issued Nov. 11, 1998 which are incorporated by reference in their entirety herein. The method and apparatus for controlling the delivered volume of fluid flow to the dynamic aortic patch is disclosed in more detail in allowed U.S. patent application Ser. No. 08/912,419 filed Aug. 18, 1997, which is incorporated by reference herein in its entirety.

Referring now to FIGS. 2–5, the patch 10 is shown in longitudinal and transverse cross-sectional views implanted within the wall of the thoracic aorta 12. The inflatable chamber 26 of the patch 10 is illustrated in an inflated condition in FIGS. 2 and 3, and illustrated in a deflated condition in FIGS. 4 and 5. To implant the device, a surgeon makes a longitudinal incision through the wall of the aorta 12, usually downwardly from a location just below the subclavian artery, and the device is placed within the incision and sutured firmly in position by sutures passing through the projecting suture flange 34 of the sheet material layer 32. The material 32 has a fibrous surface into which body tissues will migrate and mechanically interweave to augment the sealing action initially established by the sutures.

As can be seen in the cross-sectional views of FIGS. 2–5, the outer side of the patch 10 as implanted is a relatively thick, semi-rigid body or shell 14 molded from a biocompatible urethane material or any suitable substitute. The shell 14 includes the projecting passage 20 formed integrally with the shell 14. As can best be seen in the plan view of FIG. 1, the shell 14 is of an elongate elliptical shape with an upper or outer surface 36 convex in both longitudinal and transverse directions. The lower or inner surface 16 of shell 14 is concave in both the longitudinal and transverse directions. Preferably, the peripheral side edge 18 is smoothly rounded throughout an entire extent.

The thin wall, flexible membrane 24 is fixedly secured to the shell 14. The flexible membrane 24 is preferably fixedly secured with respect to the outer surface 36 adjacent the peripheral side edge 18. Preferably, the membrane 24 is free from the peripheral side edge 18 and free from the inner surface 16 of the shell 14. For purposes of illustration, membrane 24 and shell 14 are illustrated as if separately formed. Preferably, the inflatable chamber 26 is formed by known techniques resulting in the membrane 24 and the shell 14 becoming in effect a single unitary structure.

By way of illustration and not limitation, a suitable forming technique can include molding the shell 14 into the form as illustrated in FIGS. 1–5, and then providing a coating of wax to entirely cover the inner surface 16 and peripheral side edge 18. The wax-coated shell 14 is then dipped into a commercially available biomer lacquer to form an enclosing layer approximately 0.012 inches thick around the wax-coated shell 14. During this process, the biomer lacquer partially dissolves the exposed, non-wax-coated (surface) of the urethane and produces an integral structure. This particular process is known as salvation bonding. The wax is subsequently melted and extracted through the passage 20, thereby establishing an enclosed lumen or air chamber in the interior of the patch 10.

As is described in greater detail in the prior patents incorporated herein by reference in their entirety, the tube is lead from the implanted patch to a percutaneous access device implanted beneath and projecting through a patient's skin. The percutaneous access device allows the tube and, preferably, electrocardiograph leads, to be operatively connected to or disconnected from an external pneumatic pump and controller. In operation, the inflatable chamber 26 is cyclically inflated and deflated with a pressurized gaseous fluid synchronously with a heartbeat of the patient. Preferably, the synchronous cyclical inflation and deflation is based on a set of programmable patient parameters relating to heart function.

Referring to FIGS. 1–6, the bladder includes a shell or body 14, a relatively thin membrane 24 and a Dacron or other suitable outer layer 32. The body 14 is a relatively thick, semi-rigid shell member 14 which is molded from a biocompatible urethane material and incorporates a projecting air inlet tube 20. The plan view of the body 14 illustrates an elongate elliptical shape. FIG. 3 is a cross-sectional view illustrating the body shape as having a convex outer surface 36 with a concave inner surface 16 which extends over the full length of the body 14. FIG. 2 is a cross-sectional view illustrating the MAV in an inflated condition, and FIG. 4 illustrates the MAV in a cross-sectional view depicting a deflated condition. The cross-sectional view of FIGS. 2 and 4 illustrates the body or shell 14 with a peripheral side edge 18 tapering at both ends to approximate the geometrical intersection of the body with a substantially circular aorta 12 in a saddle like configuration. The Dacron velour, or other suitable material, layer 32 is bonded to the outer surface 36 of the body 14 to provide a freely projecting flange 34 used for suturing the device in place after an incision has been made in the aorta 12.

The peripheral side edge 18 is smoothly rounded throughout an entire extent to minimize local flexing stress particularly when the bladder membrane 24 is pulled snugly over the edge at the mid-body portion or membrane tension zone 30 during the deflation cycle. The thin wall flexible membrane 24 is a biomer produced by the technique described in U.S. Pat. No. 4,630,597 (solvation bonding) which is incorporated herein by reference in its entirety, and is formed using a mandrel having a "waist" or gradual narrowing of the elongate portion to form a waist as described in greater detail below. The desired shaping concept according to the present invention can best be seen in FIGS. 6 and 7 with the ratio of elongate width to waist exaggerated for clarity.

Figure 8:
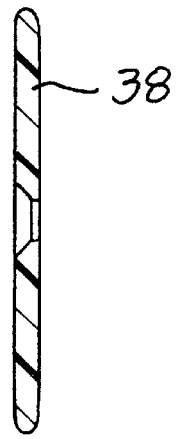
FIG. 8 is a cross-sectional view of the mandrel taken as shown in FIG. 7.
Figure 9:
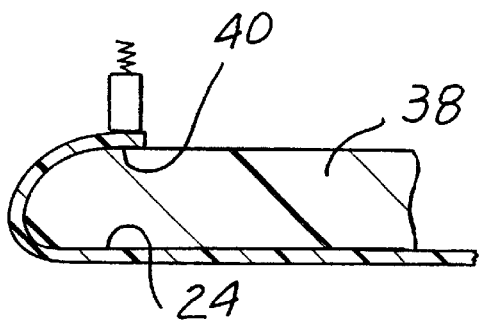
FIG. 9 is a detail view of an edge of the mandrel with a flexible membrane wrapped around the edge and held in place by at least one clip shown in phantom.

The shaped dimension of the mandrel 38 illustrated in FIGS. 7–9 enables a membrane 24 to be formed with an outer land 40 adapted to fit around the peripheral side edge 18 of the shell body 14 and extends onto the convex surface 36 to form a bonding flange enabling the membrane 24 to be permanently fastened to the body 14 to effectively form a single unitary structure. The transverse sizing of the membrane 24 is chosen to allow free conformability under aortic blood pressure with the convex or inner surface 16 of the shell body 14 at the elliptical end portions 42, 44. The membrane 24 at these two ends 42, 44 is sized to prevent being placed in arcuate tension when the membrane 24 is in restrained contact with the peripheral side edge 18. Simultaneously in the mid section or membrane tension zone 30 bounded by the elliptical ends 42, 44, the waist narrowing feature creates a gradually increasing extent of contact restraint between the membrane 24 and the peripheral side edge 18 as the extensible membrane 24 is driven toward the concavity. The membrane 24 is placed in increasing tension as the arcuate cord length decreases toward the mid-body waist 28 until equilibrium between membrane 24 restorative forces and aortic blood pressure is achieved. The membrane motion is arrested in equilibrium prior to contacting the mid-body concavity forming a chamber portion resistant to collapse as the enclosed inflatable chamber 26 is deflated. The collapse resistant portion of the inflatable chamber 26 has a total volume creating negligible reduction in total displacement and prevents the air outlet passageway 20 from being occluded or in the extreme assures that any occlusion, occurs after all the air in the bladder has been exhausted. The tendency of the membrane waist in tension to deform the semi-rigid shell body 14 is countervailed by the prevailing blood pressure in the aorta 12.

During a deflation cycle, pressurized fluid is not trapped in the elliptically tapered end portions 42, 44 of the bladder and compressed fluid in the elongate mid-section is progressively squeezed out from both sides by virtue of membrane tension decreasing as a function of distance from the midpoint or waist where the compressed fluid outlet 20 is located. The membrane waist tension local to the elliptical ends 42, 44 is low but still effective enough to induce complete exhausting of compressed fluid to proceed from the tip of the bladder toward the outlet passage 20. The membrane septum surface in deflation is shown in FIG. 6 and defined by the pattern illustrating tensile distortion in the waist zone.

The membrane length illustrated in FIGS. 3 and 5 demonstrates the membrane 24 and shell body 14 conformance in the waist tension zone 30. The membrane transverse length at rest, is less than the inner circumference of the body concavity and (with a stretch factor based on tensile modulus factored into the waist dimension) the membrane 24 will normally be forced into intimate contact with the body concavity under aortic blood pressure during the deflation cycle. Under normal operating conditions and aortic blood pressure, the membrane 24 in the waist zone is the last portion of the membrane to seat against the shell concavity at the end of the deflation cycle. When the membrane is caused to seat against the shell concavity in the waist zone, the aortic hydraulic forces will still be partially neutralized by tensile restorative forces built up in the stretched membrane 24.

Under the conditions of partial or full seating as described above, the membrane impact velocity against the shell concavity will be reduced. Consequently, membrane life may be increased and patient comfort improved by a reduction in the deflation "thumping" action. The inflation cycle illustrated in FIGS. 2 and 3 produces the expected prolate bulging into the aorta with a slight loss of displacement due to a reduction of the transverse membrane length in the waist zone and the associated bulging component. The slight loss of displacement can be accepted or can be compensated for by increasing inflation pressure.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus comprising:

an elongate semi-rigid shell having an inner surface terminating in a peripheral side edge and at least one passage extending through the shell to define an opening in the inner surface; and an elongate, flexible membrane connected to the shell adjacent to the peripheral side edge and defining an enclosed inflatable chamber in fluid communication with the passage, said membrane having a centrally located higher tension zone adjacent the opening of the passage through the shell where tension decreases with respect to distance from the at least one passage to prevent occluding the entrance while deflating the chamber.

2. The apparatus of claim 1 further comprising:

the passage disposed adjacent a midway portion of the shell.

3. The apparatus of claim 2 further comprising:

the reduced dimension of the membrane being a reduced waist portion disposed adjacent to the midway portion of the shell when attached thereto.

4. The apparatus of claim 1 further comprising:

the membrane continuously bonded to an outer surface of the shell adjacent the peripheral edge.

5. The apparatus of claim 1 further comprising:

the inner surface of the shell being contoured and concave in shape.

6. The apparatus of claim 1 further comprising:

the membrane being formed of a thin, flexible, heat setable, material.

7. An apparatus for assisting cardiac function during a cardiac cycle of a patient when positioned with respect to an aorta, the apparatus comprising:

an elongate semi-rigid shell having a contoured, concave inner surface terminating at a peripheral side edge;

at least one passage extending through the shell to define an opening in the inner surface; and an elongate, flexible membrane connected to the shell adjacent to the peripheral side edge and defining an enclosed inflatable chamber in fluid communication with the passage, said membrane having a centrally located higher tension zone adjacent the opening of the passage through the shell where tension decreases with respect to distance from the at least one passage to prevent occluding the entrance while deflating the chamber.

8. The apparatus of claim 7 further comprising:

the passage disposed adjacent a midway portion of the shell.

9. The apparatus of claim 8 further comprising:

the reduced dimension of the membrane being a reduced waist portion disposed adjacent to the midway portion of the shell when attached thereto.

10. The apparatus of claim 7 further comprising:

the membrane continuously bonded to an outer surface of the shell adjacent the peripheral edge.

11. The apparatus of claim 7 further comprising:
the membrane being formed of a thin, flexible, heat setable, material.

12. The apparatus of claim 7 further comprising:
a thin sheet material connected to an outer surface of the shell and extending beyond the peripheral side edge to define a suture flange for attaching the shell to an aorta of a patient.

13. The apparatus of claim 12 further comprising:
the thin sheet material bonded to a substantial portion of the outer surface of the shell.

14. The apparatus of claim 12 further comprising:
the thin sheet material being Dacron velour material.

15. A dynamic aortic patch having a flexible membrane and manufactured according to a method including the steps of providing an elongate mandrel having a shape defined by substantially flat major surfaces opposite one another and terminating at a rounded peripheral side edge extending between the major surfaces, the side edge contoured and curved to define partial ellipses at both ends and a reduced waist portion adjacent a midway portion, placing a thin, flexible, heat setable, membrane over one of the flat major surfaces and wrapped around the side edge a sufficient distance to form a flange adjacent the opposite flat major surface, holding the membrane in place on the mandrel with at least one clip, and heating the membrane sufficiently to set in memory of the membrane a shape of the mandrel, the dynamic aortic patch comprising:

an elongate semi-rigid shell having an inner surface terminating in a peripheral side edge and at least one passage extending through the shell to define an opening in the inner surface; and an elongate, flexible membrane connected to the shell adjacent to the peripheral side edge and defining an enclosed inflatable chamber in fluid communication with the passage, said membrane having a centrally located higher tension zone adjacent the opening of the passage through the shell where tension decreases with respect to distance from the at least one passage to prevent occluding the entrance while deflating the chamber.

16. The dynamic aortic patch of claim 15 further comprising:
the flange of the membrane bonded to an outer surface of the elongate semi-rigid shell.

17. The dynamic aortic patch of claim 16 further comprising:
the flange bonded continuously adjacent the peripheral side edge of the shell to define an inflatable chamber in fluid communication with the passage through the shell.

18. The dynamic aortic patch of claim 15 further comprising:
a thin sheet material bonded on a substantial portion of an outer surface of the shell and extending beyond the peripheral side edge of the shell to define a suture flange for attaching the shell to an aorta of a patient.

19. An apparatus comprising:

an elongate semi-rigid shell having an inner surface terminating in a peripheral side edge and at least one passage extending through the shell to define an opening in the inner surface; and a flat-surfaced, reduced-waist-contoured, mandrel-formed, elongate, flexible membrane connected to the shell adjacent to the peripheral side edge and defining an enclosed inflatable chamber in fluid communication with the passage, said membrane having a centrally located higher tension zone adjacent the opening of the passage through the shell where tension decreases with respect to distance from the at least one passage to prevent occluding the entrance while deflating the chamber.

* * * * *